United States Patent [19]

Morrison

[11] Patent Number: 5,569,247
[45] Date of Patent: Oct. 29, 1996

[54] ENHANCED VARIABLE ANGLE BONE BOLT

[75] Inventor: Matthew M. Morrison, Memphis, Tenn.

[73] Assignee: Smith & Nephew Richards, Inc., Memphis, Tenn.

[21] Appl. No.: 411,531

[22] Filed: Mar. 27, 1995

[51] Int. Cl.⁶ .................................................. A61B 17/56
[52] U.S. Cl. ........................... 606/61; 606/60; 606/72; 606/73
[58] Field of Search ............................. 606/60, 61, 72, 606/73, 69

[56] References Cited

U.S. PATENT DOCUMENTS

| | | | |
|---|---|---|---|
| 1,077,046 | 10/1913 | Dodds | 411/397 |
| 5,129,899 | 7/1992 | Small et al. | 606/61 |
| 5,176,679 | 1/1993 | Lin | 606/61 |
| 5,196,014 | 3/1993 | Lin | 606/61 |
| 5,330,474 | 7/1994 | Lin | 606/61 |
| 5,443,467 | 8/1995 | Biedermann et al. | 606/72 |

Primary Examiner—Michael Powell Buiz
Assistant Examiner—Mark S. Leonardo
Attorney, Agent, or Firm—Pravel, Hewitt, Kimball & Krieger

[57] ABSTRACT

An improvement to a multi-angle fastener for use in connecting a bone portion with a connecting member. The multi-angle fastener includes a rotating member having a central longitudinal axis and an outer surface; a fixed member having a central longitudinal axis and an outer surface having threading configured to be surgically implantable into a patient's bone tissue; and a joint for connecting the rotating and fixed members together. The joint including corresponding mating surfaces configured to articulate with each other sufficiently to allow the rotating and fixed members to angle relative to one another. The improved mating surfaces comprising a tapered flange and a corresponding tapered groove respectively configured to allow for increased fatigue resistance of the fastener when the rotating and fixed members are secured together.

6 Claims, 4 Drawing Sheets

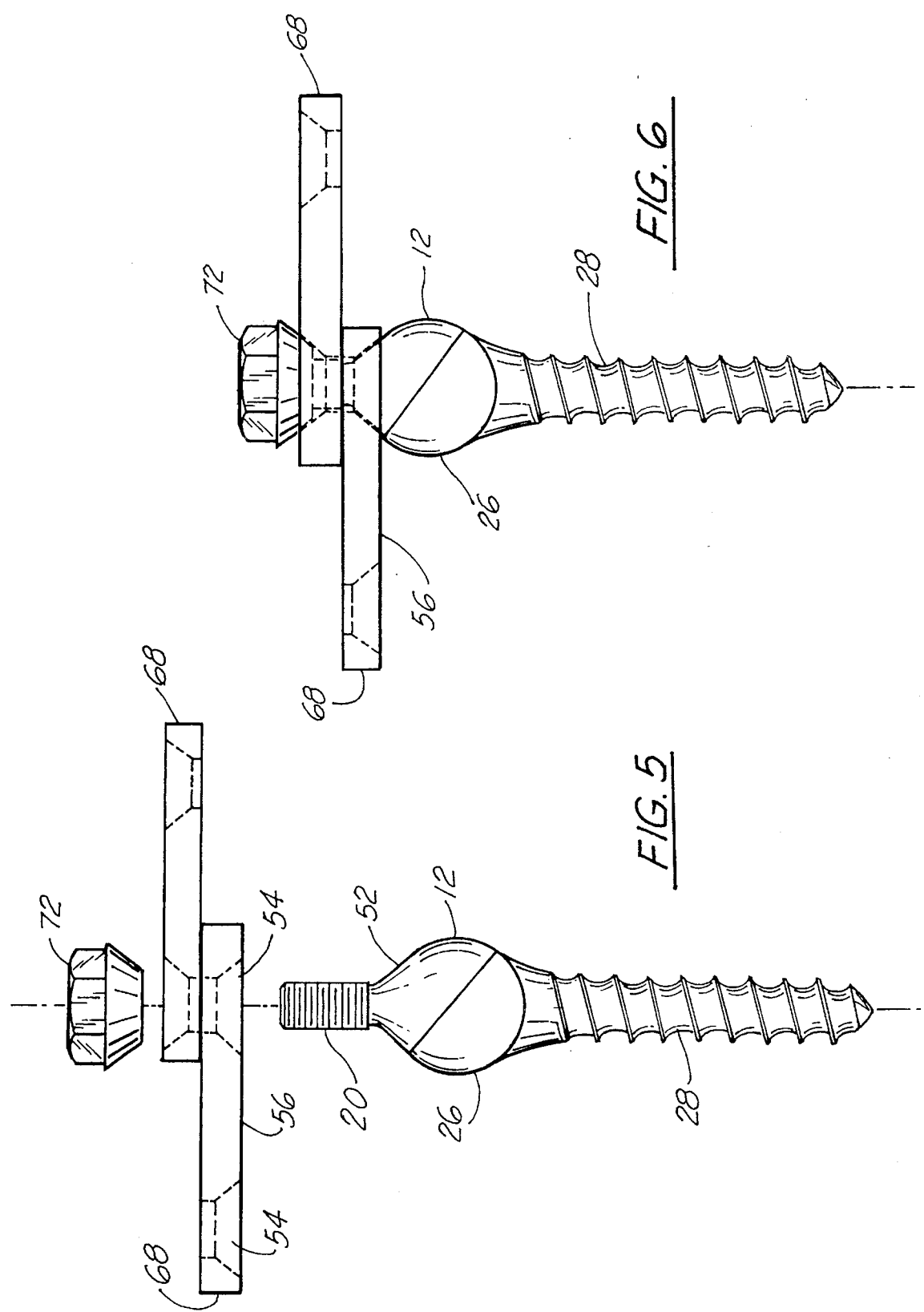

ENHANCED VARIABLE ANGLE BONE BOLT

SPECIFICATION

1. Field of the Invention

The present invention relates to orthopedic surgery and more particularly to an improved bone bolt for implanting in bones of a human patient wherein the bone bolt is formed from two section so as to allow for a variation in angulation between the sections with an improved connection between the two bolt sections.

2. Background of the Invention

There are a number of surgical procedures which require the fixation of bones such as spinal fixation of portions of the spine with respect to one another or fixation of bone fragments as a result of trauma. Typically, bone bolts or screws and bone plates or spinal rods are employed in the fixation of bones wherein the bone bolts or screws are implanted in a surgical procedure involving the formation of a series of surgical openings in adjacent portions of the spine or along a bone section, for implanting the threaded bone bolts or screws. Connective structures such as rods or plates extend between the various spine members or the bone fragments and are connected to the implanted bolts or screws with connector devices.

A U.S. pat. No. 4,369,769 to Edwards shows a spinal fixation system using elongated rods to bridge across various portions of the spine. In the Edwards '769 patent, a spinal fixation device is provided in which sleeves or spacers are placed over and around spinal rods in order to obtain a better reduction of spinal fractures or spinal deformities. These sleeves can be made into various thicknesses so that the surgeon can obtain optimum fixation in each case.

Use of bone screws in connecting rods is also seen in the Ulrich et al. U.S. Pat. No. 4,433,677 entitled "Implantable Splint for Correction of Lumbosacral Spondylodesis." In the Ulrich patent, a spinal distraction splint has two like anchor screws extending along respective longitudinal screw axes and adapted to be anchored in the pelvis with the axes crossing. Each of the screws has a head formed with a transverse open recess centered on respective transverse axis and with an angular array of teeth centered on and angularly spaced about the respective transverse axis.

A U.S. pat. No. 4,611,581 to Steffee entitled "Apparatus for Straightening Spinal Columns" provides an apparatus to reduce the extent of displacement between adjacent vertebrae and a person's spinal column and to subsequently maintain the vertebrae in a reduced displacement relationship. When the apparatus is to be installed, holes are formed in the displaced vertebrae and in vertebrae on opposite sides of the displaced vertebrae. Force transmitting members (bone bolts) are mounted in the holes in the vertebrae. A spinal plate is then positioned on the spinal column with the bone bolts extending outwardly through the slots in the spinal plate. Nuts are tightened on the bone bolt members connected with vertebrae on opposite sides of the displaced vertebrae to anchor the spinal plate in place. A nut on the extending bone bolt is then tightened to hold the displaced vertebrae in the desired position. Connectors for attaching the rods or plates to vertebrae of a spinal column are known in the art, for example such as those described in U.S. pat. No. 5,209,752 and 5,296,014.

When doctors use a plurality of bone bolts implanted in a series of bolts, and desire a connection of the series, it is frequently difficult to make a tight connection because of the non-alignment of the series. For example, in a spinal construct where bone bolts are placed in several adjacent vertebral pedicles, the adjacent bone bolts will almost never align themselves such that a plate or rod may be connected to them. The adjacent bone screws are usually independently located with respect to each other in three dimensional space, which creates an offset distance of some kind between the bolt and the plate/rod connection. The offset problem has been addressed by providing connectors that accommodate the differences of the adjacent bolts implanted in a series. However, there is a limit to the adjustability of the currently available connectors when used with traditional bone bolts and bone screws.

Bone bolts have been provided in which the bolt is formed from two sections so as to allow for a certain amount of angulation of the two sections when implanted in a patient's bone tissue. However, problems have been encountered in the connection between the upper and lower sections which results in a desrease in fatigue resistance and torsional stability.

There is a need for a variable angle bone bolt which has an improved connection between the upper and lower sections in order to provide for torsional stability and increased fatigue resistance while still allowing for a variation in angulation of the sections.

SUMMARY OF THE INVENTION

The object of the invention is to provide an improved connection for a two sectional bone bolt that allows for a variation in angulation of the two sections. The enhanced bole bolt includes a multi-angle fastener for use in connecting a bone portion with a connecting member having a rotating member and a fixed member. The rotating member has a central longitudinal axis and an outer surface; the fixed member has a central longitudinal axis and an outer surface with a bone attachment means configured to be surgically implantable into a patient's bone tissue; and a joint for connecting the rotating and fixed members together. The joint includes corresponding mating surfaces configured to articulate with each other sufficiently to allow the rotating and fixed members to angle relative to one another. The enhanced mating surfaces includes a tapered flange and a corresponding tapered groove respectively configured to allow for increased fatigue resistance of the fastener when the rotating and fixed members are secured together. The rotating and fixed members also angle and rotate relative to one another prior to securing the rotating and fixed members together.

BRIEF DESCRIPTION OF THE DRAWINGS

For a further understanding of the nature and objects of the present invention, reference should be made to the following detailed description taken in conjunction with the accompanying drawings, in which like parts are given reference numerals and wherein:

FIG. 5 is an exploded elevational view of the bone bolt in FIG. 1 in use with stacked bone plates and a washer;

FIG. 6 is a elevational view of the construct of FIG. 5 after assembly;

DETAILED DESCRIPTION OF PREFERRED EMBODIMENT

Figure 1:
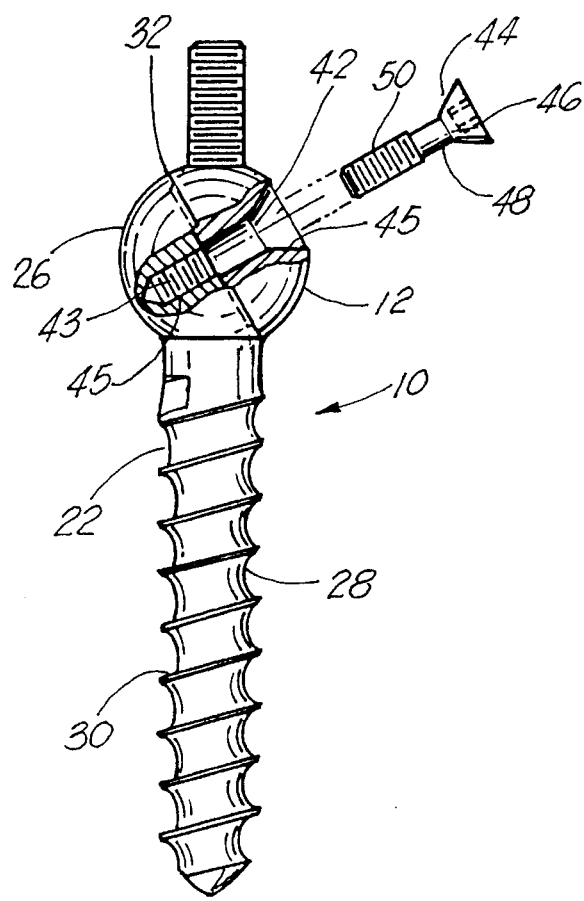
FIG. 1 is a partial sectional view of the bone bolt of the present invention.
Figure 2:
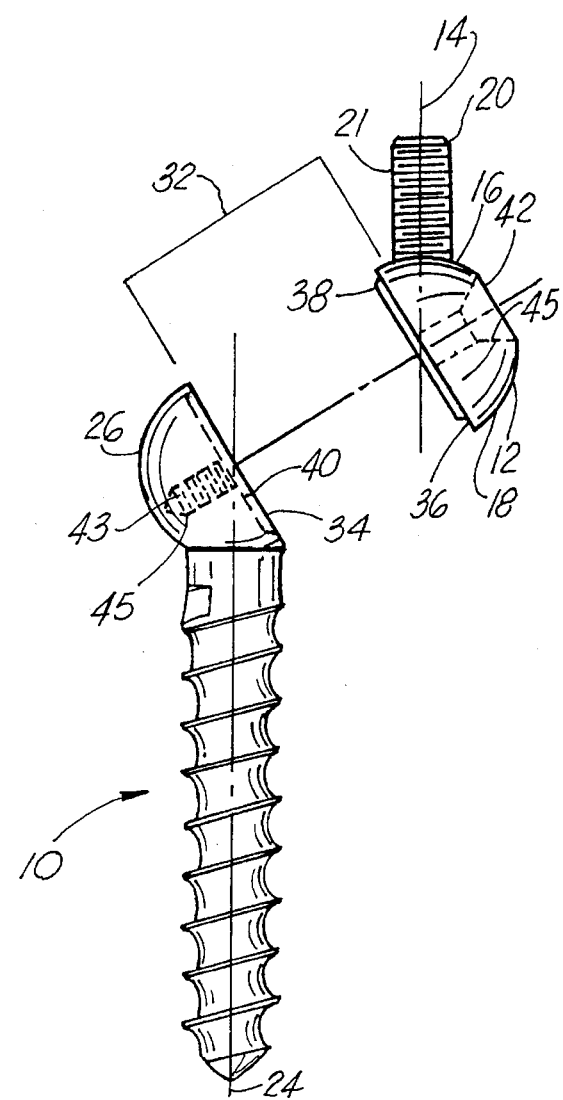
FIG. 2 is an exploded view of the bone bolt of the present invention as seen in FIG. 1.
Figure 3:
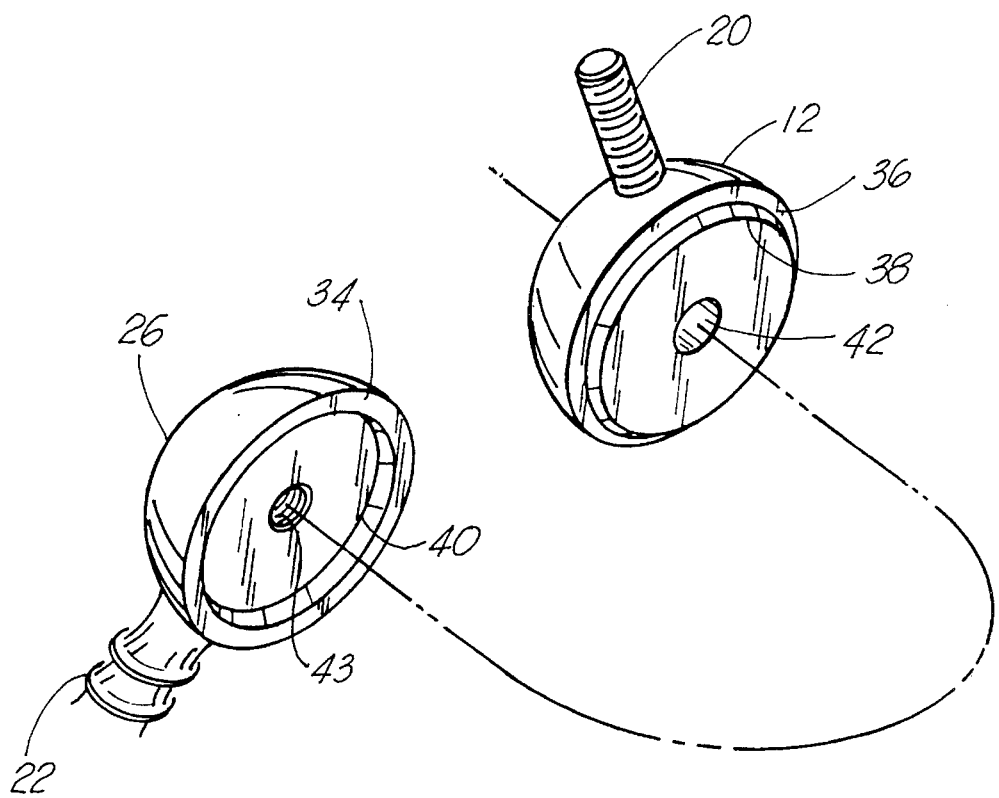
FIG. 3 is a exploded partial view of the bone bolt of the present invention as seen in FIG. 1.
Figure 7:
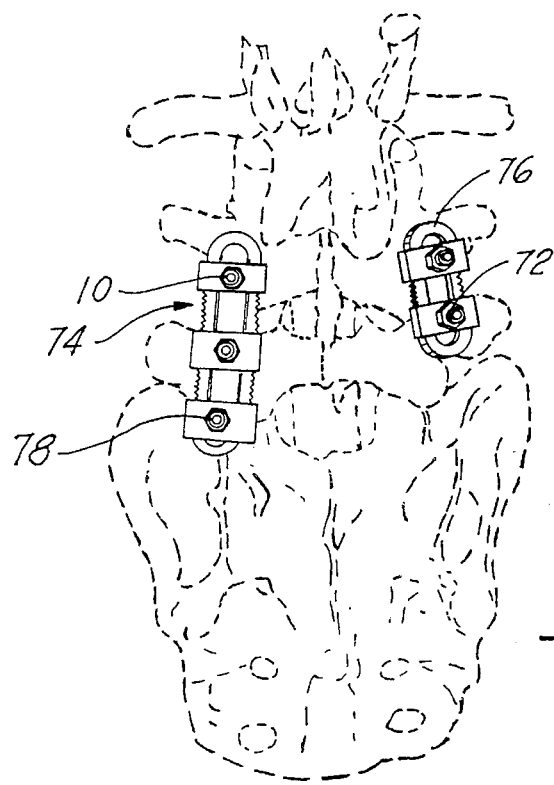
FIG. 7 is a schematic view illustrating the enhanced bone bolt of the present invention implanted in a human patient as part of a spinal plate fixation system.

The improved or enhanced bone bolt of the present invention is shown in FIGS. 1 and 2 as fastener 10 having an rotating member 12 and a fixed member 22. Rotating member 12 has a central longitudinal axis 14, a proximal end 16, a distal end 18, and an outer surface that is generally in the shape of one half of a sphere. Rotating member 12 includes a projection 20 at the proximal end 16 that is generally cylindrical in shape with a threaded outer surface 21 configured to mate with a securing device such as a nut 72 (FIGS. 6, 7 and 8) when used with a bone fixation system such as bone plate 68 or 74 as illustrated in FIGS. 5, 6 and 7. Fixed member 22 has a central longitudinal axis 24, a proximal end 26 that is generally in the shape of one half of a sphere, and a distal shaft end 28. Shaft end 28 has bone attachment means, such as a threaded outer surface 30, configured to be surgically implantable into a patient's bone tissue. As shown in FIG. 1, a sphere is formed when rotating member 12 and the proximal end 26 of fixed member 22 are joined together.

When joined, the two members 12, 22 form a joint 32 with mating surface 34 on proximal end 26 and a mating surface 36 on rotating member 12. Mating surface 36 has a tapered flange 38 and mating surface 34 has a corresponding tapered groove 40 which allows rotating member 12 to angle and rotate relative to the fixed member 22 prior to being secured together. Flange 38 and groove 40 are tapered at an angle of about between 2°–10° which provides a self-locking mechanism for mating surfaces 34, 36 when connected. The corresponding mating surfaces 34, 36 of the members 12, 22 are angled generally between about 25°–65° relative to the central longitudinal axes 14, 24 of rotating and fixed members 12, 22. The tapered flange 38 and groove 40 improves the fatigue resistance and thus the fatigue life of fastener 10 by altering the bending load on fastener 10 when implanted in bone tissue. The mating flange 38 and groove 40 distributes the bending load placed on the implanted fastener 10 to the outside edges of mating surfaces 34, 36 of fastener 10. Evenly distributed tension is created by the flange 38 and groove 40 connection of the mating surfaces 34, 36 which displaces the bending load, thus allowing for more torsional stability and fatigue resistance than present with other multi-sectional fasteners of a similar design.

Fastener 10 has an opening 42 extending through joint 32 between about a 25°–65° angle relative to the central longitudinal axes 14, 24 of the fastener 10. Opening 42 extends through rotating member 12 and terminates a distance within fixed member 22, as shown in FIGS. 1 and 2. Opening 42 has an inner surface 45 that is conical in shape at the at the surface of the rotating member 12 that changes in to a cylindrical shape as shown in FIGS. 1 and 2. The portion of opening 42 that terminates in fixed member 22 includes threading 43 on the inner surface 45. A connector 44, generally in the shape of a set screw or shoulder bolt, is configured to fit opening 42 for holding the rotating member 12 and fixed member 22 together at joint 32. As shown in FIG. 1, the connector or set screw 44 includes a head 46 which is generally conical in shape, a shaft portion 48 and a threaded portion 50. The shaft portion 48 is generally the diameter of the minor diameter of the threaded portion 50. Threaded portion 50 is configured to engage threading 43 on the inner surface 45 of opening 42.

Figure 4:
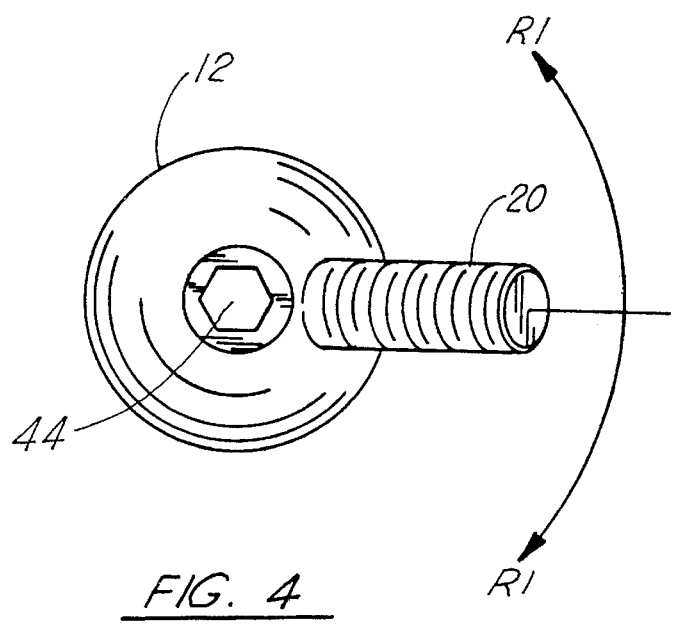
FIG. 4 is a top plan view showing the angulation of the bone bolt of the present invention as seen in FIG. 1.

The joint 32 of fastener 10 allows the rotating member 12 to angle and rotate relative to the fixed member 22 prior to insertion and tightening of the set screw 44. The range of angularion is between about 25 °–65° relative to the central longitudinal axes 14, 24 of rotating and fixed members 12, 22. The range of rotation is illustrated as R1-R1 in FIG. 4.

Alternatively, fastener 10 can include a tapered proximal portion 52 on rotating member 12. The tapered proximal portion 52 is configured so as to abut a conically shaped opening 54 on a lower surface 56 of a bone plate 58, as illustrated in FIGS. 5, 6 and 7 or a rod/bolt connector 70 as shown in FIG. 8.

Figure 8:
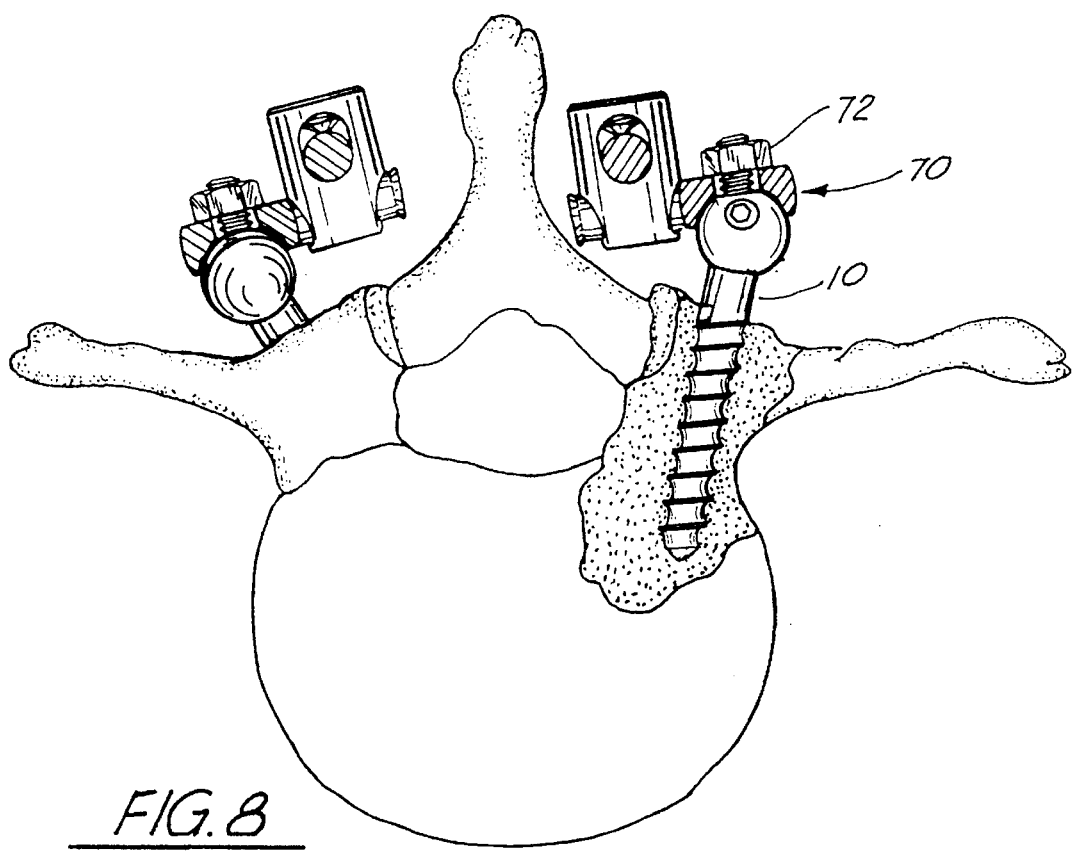
FIG. 8 is a fragmentary partial cross sectional view of a vertebrae illustrating the present invention implanted in a human patient as part of a spinal rod fixation system.

Fastener 10 can be used with a bone plate 74 construct as shown in FIG. 7 which includes a bone plate 76 and fasteners 78 or with a spinal rod/bolt construct 70 as shown in FIG. 8. Alternatively, fastener 10 can be used in any bone fixation system where bone portions are being surgically fixed with a plate or other connecting member.

It should be understood that there can be improvements and modifications made to the embodiments of the invention described in detail above without departing from the spirit or scope of the invention, as set forth in the accompanying claims.

What is claimed is:

1. A multi-angle fastener for use in connecting a bone portion with a connecting member, said multi-angle fastener comprising a rotating member having a central longitudinal axis and an outer surface; a fixed member having a central longitudinal axis and an outer surface having a bone attachment means configured to be surgically implantable into a patient's bone tissue; and joint means for connecting the rotating and fixed members together, said joint means including corresponding mating surfaces configured to articulate with each other sufficiently to allow the rotating and fixed members to angle relative to one another, the mating surfaces forming enhanced mating surfaces comprising:

tapered flange and a corresponding tapered groove respectively configured to allow for increased fatigue resistance of the fastener when the rotating and fixed members are secured together, said rotating member having a tapered portion configured to abut a lower surface of a bone plate member.

2. The fastener of claim 1, wherein the mating surfaces are further configured to allow the rotating and fixed members to angle and rotate relative to one another prior to securing the rotating and fixed members together with the angulation being in a range of about between 20–70 degrees relative to the central longitudinal axes of the rotating and fixed members.

3. The fastener of claim 1, further including an opening extending through the joint means and a connector configured to fit the opening for holding the rotating and fixed members together at the joint means, said joint means having corresponding mating surfaces angled relative to the central longitudinal axis of the rotating and fixed members.

4. The fastener of claim 3, wherein the connector is a screw connection having a threaded portion and a shaft portion.

5. The fastener of claim 1, further including a spinal fixation system having the combination of a connecting member such as a bone plate member and a plurality of bone attachment members for securing the bone plate member to a patient's bone tissue wherein the fastener of claim 1 is used as one of the bone attachment members.

6. The fastener of claim 1, further including a spinal fixation system having the combination of a spinal rod connected to connecting members such as a plurality of rod/bolt connectors for connecting the spinal rod to a patient's bone tissue wherein the fastener of claim 1 is used to secure at least one of the rod/bolt connectors to the patient's bone tissue.

\* \* \* \* \*